United States Patent
Aitchison (10) Patent No.: US 8,382,909 B2
(45) Date of Patent: Feb. 26, 2013

(54) USE OF SPECTROSCOPIC TECHNIQUES TO MONITOR AND CONTROL REACTANT GAS INPUT INTO A PRE-PUMP REACTIVE GAS INJECTION SYSTEM

(75) Inventor: Kenneth Allen Aitchison, Los Gatos, CA (US)

(73) Assignee: Edwards Limited, Crawley, West Sussex (GB)

(*) Notice: Subject to any disclaimer, the term of this patent is extended or adjusted under 35 U.S.C. 154(b) by 2334 days.

(21) Appl. No.: 11/285,810

(22) Filed: Nov. 23, 2005

(65) Prior Publication Data
US 2009/0320881 A1 Dec. 31, 2009

(51) Int. Cl.
*B08B 7/04* (2006.01)
*B08B 7/00* (2006.01)
(52) U.S. Cl. ............ 134/18; 134/22.18; 134/37
(58) Field of Classification Search ............ 134/18, 134/1, 1.1, 22.1, 22.18, 22.11, 22.12, 37; 438/905
See application file for complete search history.

(56) References Cited

U.S. PATENT DOCUMENTS

| 5,207,836 A | 5/1993 | Chang |
| 5,565,038 A | 10/1996 | Ashley |
| 5,766,360 A * | 6/1998 | Sato et al. .............. 118/666 |
| 6,874,511 B2 | 4/2005 | Kutsch et al. |

OTHER PUBLICATIONS

PCT Notification of Transmittal of the International Search Report and the Written Opinion of the International Searching Authority, or the Declaration of International Application No. PCT/US06/44996; Date of mailing: May 21, 2008.
PCT International Search Report of International Application No. PCT/US06/44996; Date of mailing of the International Search Report: May 21, 2008.
PCT Written Opinion of the International Searching Authority of International Application No. PCT/US06/44996; Date of mailing: May 21, 2008.

* cited by examiner

*Primary Examiner* — Alexander Markoff (57) ABSTRACT

The present invention relates to vacuum processing systems in which process gases are introduced in a process chamber and are exhausted through a vacuum processing system exhaust path. Deposits made by the exhausted gas are reduced or eliminated by introducing a reactive gas upstream of the device affected by deposits. The amount of introduced reactive gas is controlled by measuring gas phase concentrations of exhausted gas components upstream and downstream of the affected device, and, from those measurements, determining whether the components are being consumed in deposits on the affected device.

11 Claims, 6 Drawing Sheets

USE OF SPECTROSCOPIC TECHNIQUES TO MONITOR AND CONTROL REACTANT GAS INPUT INTO A PRE-PUMP REACTIVE GAS INJECTION SYSTEM

FIELD OF THE INVENTION

The present invention relates generally to the field of high vacuum processing using process gases, and more particularly, to controlling a buildup of deposits from one or more components of the process gases on devices in the vacuum processing system exhaust path.

BACKGROUND OF THE INVENTION

Certain research and manufacturing processes require the use of a process chamber with high vacuum. For example, in semiconductor wafer processing, vacuum is used during many thin-film deposition and etching operations, primarily to reduce contamination. In such processes, pumps capable of producing a "high vacuum" of $10^{-6}$ Torr or lower are useful to assure adequate pumping speed at process pressure, and to allow for a low base pressure for cleanup between steps.

Several currently-available vacuum pump configurations are capable of producing and maintaining a high vacuum. Roots vacuum pumps and hook and claw vacuum pumps include two precisely machined rotors that rotate with equal speed in opposite directions, trapping gas in an exhaust portion of the casing and forcing it to an exhaust port. Roots and hook and claw vacuum pumps are used as primary vacuum pumps and as backing pumps. Another vacuum pump configuration capable of maintaining a high vacuum is the turbomolecular vacuum pump, which relies on the high-speed rotation of rotor vanes in close proximity to stator vanes to induce molecular movement of the gas.

In each of the above cases, the pump inlet may open directly to the process chamber or may communicate with a process chamber through a foreline. The vacuum processing exhaust path may include a backing pump in a downstream position in the vacuum processing system exhaust path for reducing a pressure drop across the primary pump. The vacuum processing system exhaust path may also include an abatement system for reclaiming, removing or neutralizing various components of the exhaust.

Figure 1:
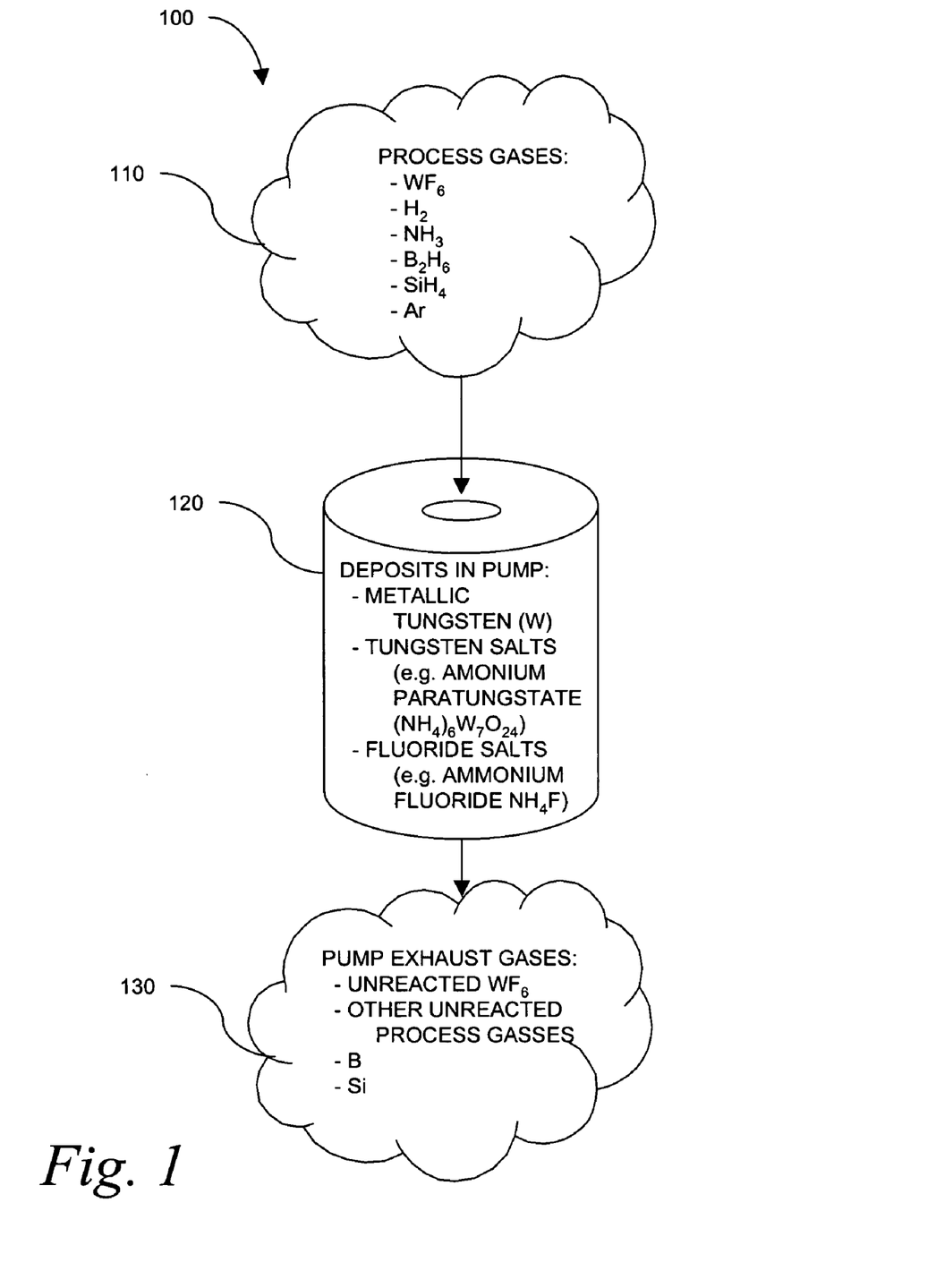
FIG. 1 is a graphical representation of a prior art vacuum process showing depositions formed in a turbomolecular pump.

One problem frequently encountered in vacuum processing systems is the deposition of solids by components of the gases passing through the vacuum processing system exhaust path. In one exemplary process 100, shown schematically in FIG. 1, the process gases 110 used in the semiconductor manufacturing process are $WF_6$, $H_2$, $NH_3$, $B_2H_6$, $SiH_4$, and Ar. $WF_6$ can react with $H_2$, $NH_3$, $B_2H_6$ and $SiH_4$ to form film deposits of metallic tungsten, tungsten salts (e.g., ammonium tungstate), or fluoride salts (e.g., ammonium fluoride). The reaction may take place in the process chamber or in various locations in the exhaust path, including the foreline, high vacuum pump 120, or in a roughing pump or abatement devices. Pump exhaust gases 130 include inert or unreacted components of the process gases, such as Ar and unreacted $WF_6$, as well as reaction products formed during deposit formation in the vacuum processing system exhaust path, such as HF, $BF_3$ and $SiF_4$.

Another mechanism that may cause deposits on surfaces along the vacuum exhaust path is the buildup of powders formed by gas phase nucleation. Gas phase nucleation results from reactions among gas phase components of the exhaust gas, resulting in a solid reaction product in powder form. That product may accumulate on surfaces with which it comes in contact. As used herein, the term "deposit" shall mean solids accumulating on surfaces in the exhaust path due to any physical mechanism, including film deposition, gas phase nucleation or other phenomenon.

However they are formed, the deposits adversely affect the performance of the vacuum pump and other devices in the vacuum processing system exhaust path. For example, solid metallic deposits on pumping elements of roots pumps and hook and claw pumps change the effective shape of the pumping elements, degrading the efficiency and effectiveness of the pump.

To address the problem of unwanted deposits on devices in the exhaust path, a carefully selected reactive gas may be injected upstream of the affected device. The reactive gas prevents the formation of deposits by reacting with the exhaust gas components.

In an example of such a technique used in the above-described vacuum process system, $NF_3$ is injected into a Remote Plasma Source (RPS) mounted in the foreline or directly at the inlet to a Roots or hook and claw pump, by means of a tee connector. The RPS is intended to dissociate the $NF_3$ into atomic fluorine which can then react with gas phase molecules to prevent deposition, or react with deposited solids to remove them. Alternatively, molecular fluorine or other fluorine-containing gases may be substituted for $NF_3$. In some cases, molecular $F_2$ alone may be used without prior RPS dissociation.

By providing a fluorine source in the foreline or at the pump inlet, the reactions that cause solid deposits are prevented or at least greatly diminished. The atomic fluorine provides a more readily available fluorine source, preventing, among other things, a reaction of $WF_6$ with the other gases or hot pump mechanisms, and thereby preventing deposition of metallic tungsten in the vacuum pump.

The fluorinated gases discussed above are generally very costly. For example, the cost of $NF_3$ in the above-described system can amount to 10% or more of the total cost of materials in a semiconductor manufacturing process. It is therefore in the interest of the practitioner to optimize the amount of reactive gas used. In some processes, the process gases are pulsed, in which case it is advantageous to pulse the fluorine source in synchronized fashion with the appropriate gas. In some cases it is desirable to maintain a flow of the fluorine source for some time after the pulse of process gas is complete.

In any case, it is desirable to have enough of the fluorinated gas present while avoiding an excess. One way to accomplish that is to experimentally pre-determine the correct ratio of fluorine source to reactive process gas. In many cases, however, the flow rate of the process gas may change, either due to aging of components or to deliberate process recipe modification. If that happens, the set point may no longer be valid, insufficient fluorine source will be delivered, and the deposition that was intended to be prevented will occur.

There is therefore presently a need to provide an improved vacuum process control incorporating a solution to the problem of accumulating deposits in the devices in the vacuum exhaust path, while controlling the cost of reactive gases used. To the inventor's knowledge, no such control is presently available.

SUMMARY OF THE INVENTION

The present invention addresses the needs described above by providing improvements to a vacuum processing system using process gases having at least one component with a tendency to produce a deposit on surfaces of a device in a vacuum exhaust path of the system. One embodiment of the system includes a reactant gas injector positioned in the vacuum exhaust path upstream of the device, the reactant gas injector capable of injecting a reactant gas into the vacuum exhaust path that reduces the tendency of at least one component to produce a deposit on surfaces of the device. The system further includes at least one sensor for measuring a concentration of the at least one component present in the vacuum exhaust path upstream of the device, and for measuring a concentration of the at least one component present in the vacuum exhaust path downstream of the device. Finally, the system includes a controller for controlling an amount of reactant gas injected by the reactant gas injector based at least in part on a difference between the upstream and downstream concentrations.

The system may be arranged with a dedicated sensor for gas concentration measurement at the upstream and downstream locations, respectively. Alternatively, the system may be arranged so that only one sensor is used. In that case, a switching mechanism may be provided that enables the sensor to be exposed at alternate times to the upstream and downstream environments of the device.

Examples of the sensors include an infrared spectrometer, a Raman spectrometer, a mass spectrometer and a laser induced fluorescence spectrometer. Other sensors may be envisioned that are able to identify at least one constituent of the gas phase on a continuous basis, and whose response can be calibrated in a quantitative manner.

The device may be a vacuum pump, or a vacuum exhaust abatement device. The component tending to form deposits may be tungsten fluoride, in which case the reactant gas is fluorine. Other applicable processes may include deposition of oxides, nitrides, silicides, borides, or other binary, ternary or quaternary solid materials.

The reactant gas injector may include a remote plasma source for dissociating a reactant gas precursor to form an atomic species of the reactant gas. Other dissociating means may alternatively be used. Further, it may be sufficient to add a reagent gas without the need for prior dissociation.

The controller may include media containing commands that, when executed, cause the controller to determine from the difference between the upstream and downstream concentrations whether at least a predetermined portion of the process gas component is being consumed in the device, and, if so, increase the amount of reactant gas injected by the injector.

In another embodiment of the invention, a method is provided for controlling deposits made by at least one component of an exhaust gas on a device in a vacuum processing system exhaust path. The method includes the steps of introducing a flow of a reactant gas into the vacuum processing system exhaust path at a position upstream of the device, the reactant gas inhibiting the deposits made by the at least one component of the exhaust gas, measuring a quantity of the at least one component of the exhaust gas present at a position upstream of the device, measuring a quantity of the at least one component of the exhaust gas present at a position downstream of the device, determining from the upstream and downstream measurements whether a portion of the at least one component of the exhaust gas is consumed in the device, and, if so, increasing the flow of the reactant gas.

The method may include the step of determining from the upstream and downstream measurements whether substantially none of the at least one component of the exhaust gas is consumed in the device, and, if so, determining whether excess reactant gas is flowing through the device, and, if so, decreasing the flow of reactant gas.

The measuring steps may include measuring the quantity of the at least one component of the exhaust gas using an instrument selected from a group consisting of an infrared spectrometer, a Raman spectrometer, a mass spectrometer and a laser induced fluorescence spectrometer.

The reactant gas may be fluorine. The step of introducing a flow of a reactant gas into the vacuum processing system exhaust path may further include dissociating a precursor gas using a remote plasma source. The reactant gas may be fluorine and the precursor gas may be $NF_3$.

The device may be selected from a group consisting of a vacuum pump and an abatement device.

The at least one component of the exhaust gas may be tungsten fluoride, in which case the reactant gas may be fluorine.

The at least one component of the exhaust gas may include at least one gas selected from the group consisting of $WF_3$, $H_2$, $NH_3$, $B2H6$ and $SiH4$. The measuring steps may include measuring a gas phase concentration of the at least one component.

Another embodiment of the invention is a vacuum processing system using process gases having at least one component with a tendency to produce a deposit on surfaces of a device in a vacuum exhaust path of the system. The system includes a reactant gas injector positioned in the vacuum exhaust path upstream of the device, the reactant gas injector capable of injecting a reactant gas into the vacuum exhaust path that reduces the tendency of the at least one component to produce a deposit on surfaces of the device by combining with the at least one component to produce a new species. The system further includes a sensor for measuring a concentration of the new species present in the vacuum exhaust path downstream of the device, and a controller for controlling an amount of reactant gas injected by the reactant gas injector based at least in part on the downstream concentration.

DETAILED DESCRIPTION OF THE INVENTION

In the present invention, a sufficient flow of fluorine source, or another reactant gas, is ensured by measuring a concentration of the process gas at the inlet and the outlet of a device such as a turbomolecular pump, and modifying the flow of the fluorine source accordingly. In a preferred embodiment, infrared spectroscopy is used to measure that concentration. While this detailed description describes the invention as relating to a system wherein the deposition of tungsten metal and other solids is reduced by the introduction of $WF_6$, it is noted that the particular reactants described are merely exemplary, and that the inventive system and method are equally applicable to other reactants.

The gas phase concentration of the process gas in question is measured at both the inlet and the outlet of the pump. In the absence of a reaction in the pump that results in deposition of tungsten, the inlet and outlet $WF_6$ signals should be equal. When reaction of $WF_6$ occurs inside the pump, $WF_6$ will be depleted from the gas phase, and the signal at the outlet will be lower than the signal at the inlet. If a fluorine source is provided in sufficient quantities to prevent this reaction, the inlet and outlet $WF_6$ signals will again be equal. By using those signals, the quantity of fluorine source may be modified to ensure that enough fluorine is provided to suppress deposition, without supplying an excess of fluorine.

Figure 2:
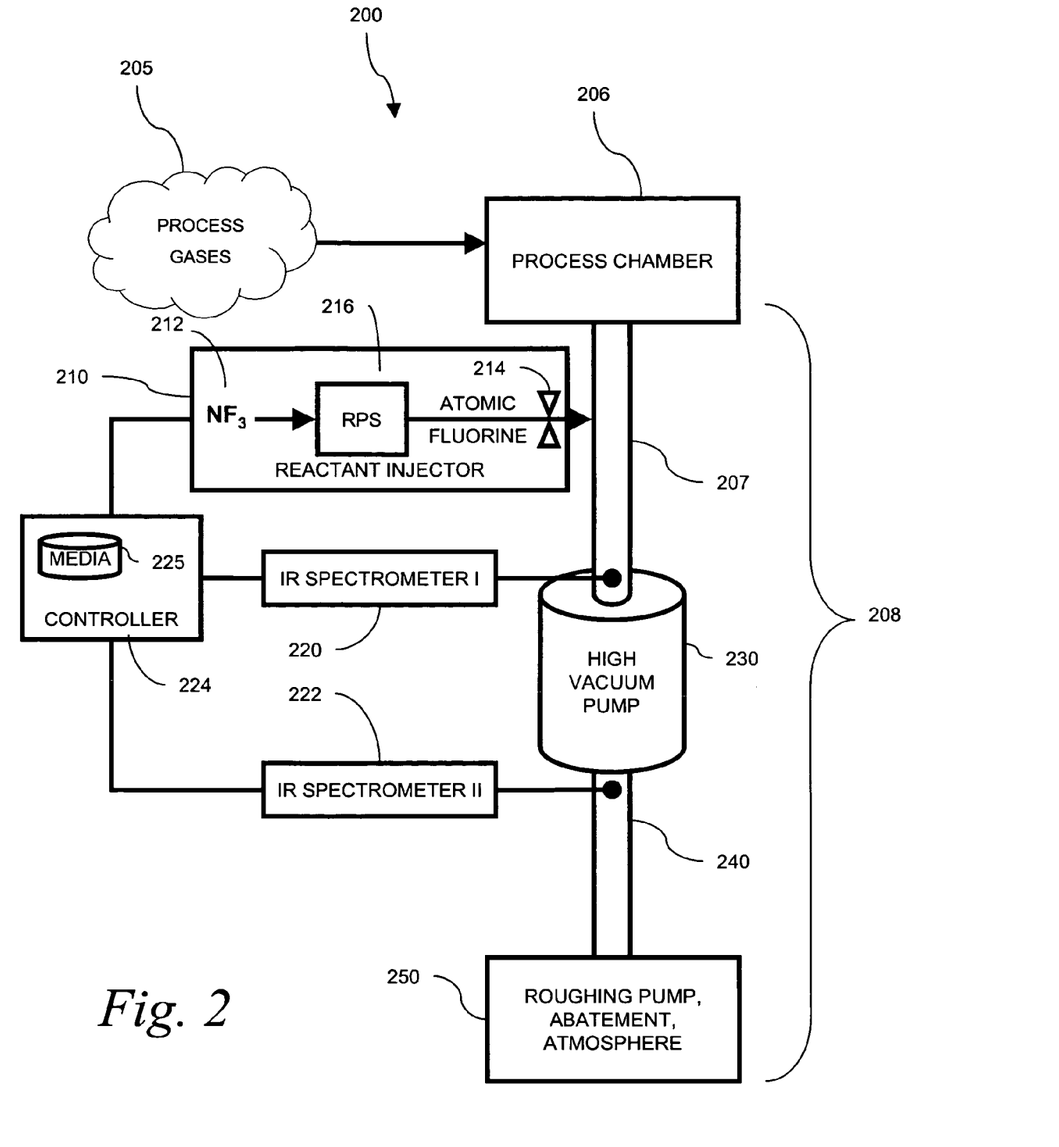
FIG. 2 is a schematic representation of a system according to one embodiment of the invention.

An exemplary embodiment 200 of such a system is shown in FIG. 2. Process gases 205 such as $WF_6$, $H_2$, $NH_3$, $B_2H_6$, $SiH_4$ and Ar are introduced into a process chamber 206. The gases may be introduced in any combination or sequence, as required in the reactions taking place in the chamber.

Evacuated gases from the process chamber 206 follow a process vacuum exhaust path 208. The path 208 may include a foreline 207 connecting a turbomolecular pump 230 with the process chamber. An additional line 240 conducts exhaust gases from the turbomolecular pump 230 to additional devices 250 such as a roughing pump and abatement chamber.

A reactant injector 210 introduces a reactant upstream of the device in which deposition is a problem; in this case, the turbomolecular pump 230. A source 212 of a precursor of the reactive gas; in this case, $NF_3$, provides the precursor gas to an RPS 216 that dissociates the $NF_3$. Techniques other than plasma, such as thermal methods, may be used to dissociate the reactive gas. Atomic fluorine is injected into the foreline 207 through an injector valve 214.

Operation of the reactant injector 210 is controlled by a programmable controller 224. The controller may control, for example, the amount of reactant gas injected and the timing of the injections.

A sensor such as the infrared spectrometer 220 is positioned to measure a gas phase concentration of one or more process gas components present in a region upstream of the device 230. An infrared spectrometer is particularly suitable for use in sensing gas phase concentrations of most gases used in semiconductor processing because those gases, such as $WF_6$, have strong infrared absorption peaks. The sensor 220 accesses the flow through a monitoring port or window in the vacuum process system exhaust path 208.

One skilled in the art will recognize that other sensors may be used to identify and quantify the presence of specific gas components at points in the process flow path. For example, in place of an infrared spectrometer, a Raman spectrometer, a mass spectrometer, or a laser induced fluorescence spectrometer may be used as one or more of the sensors of the invention. Alternatively, non-spectroscopic techniques such as electrochemical techniques or chemical sensors may be used. The sensor must be capable of identifying at least one constituent of the gas phase on a continuous basis, and have a response that may be calibrated in a quantitative manner.

Another sensor 222, such as a second infrared spectrometer, measures a gas phase concentration of the same one or more process gas components in a region downstream of the device 230. In a preferred embodiment of the invention, the second sensor 222 is of a type similar to the first sensor 220. In that way, environmental variables affect the sensors similarly, canceling systematic measurement errors. Each of the sensors 220, 222 is in communication with the controller 224.

While two separate infrared spectrometers 220, 221 are shown for monitoring gas phase concentrations upstream and downstream of the device 230, a single sensor may instead be used in conjunction with a switching mechanism (not shown) for alternatively routing to the sensor a sample from either the upstream or the downstream location. That solution has the advantages of reduced instrumentation costs and elimination of calibration errors caused by differences between the two sensors.

By comparing readings from the two sensors 220, 222, the controller 224 can determine whether all of a particular component of the exhaust gas entering the device, exits the device. A decrease in gas phase concentration of the component across the device indicates that some of the gas is being consumed in the device, presumably in the formation of deposits in the device. In such a case, the controller 224 would increase a quantity of reactant gas injected by the injector 210. The availability of reactant gas in the device would inhibit the reactions in the device that result in the deposition of solids. That control cycle is repeated until a comparison of sensor readings indicates that none of the process gas is being consumed in the device 230.

It is noted that, although the sensors 220, 222 are shown monitoring $WF_6$ concentration on either side of a high vacuum pump 230, gas phase concentration may alternatively be monitored on either side of another device or group of devices. For example, in the vacuum processing system 300 shown in FIG. 3, a reactant injector 310 introduces a reactant gas into a foreline 307 connecting a process chamber 306 and a vacuum pump 330, as in the previous example. In this case, however, the gas phase concentration of the process gas component is sampled from passageways 340, 341 in the exhaust path 308 on either side of the roughing pump and/or abatement equipment 350. In that way, deposition in the equipment 350 is detected. As in the above example, the flow of reactant gas through the reactant injector 310 is controlled by a controller 324 to minimize depositing.

Figure 3:
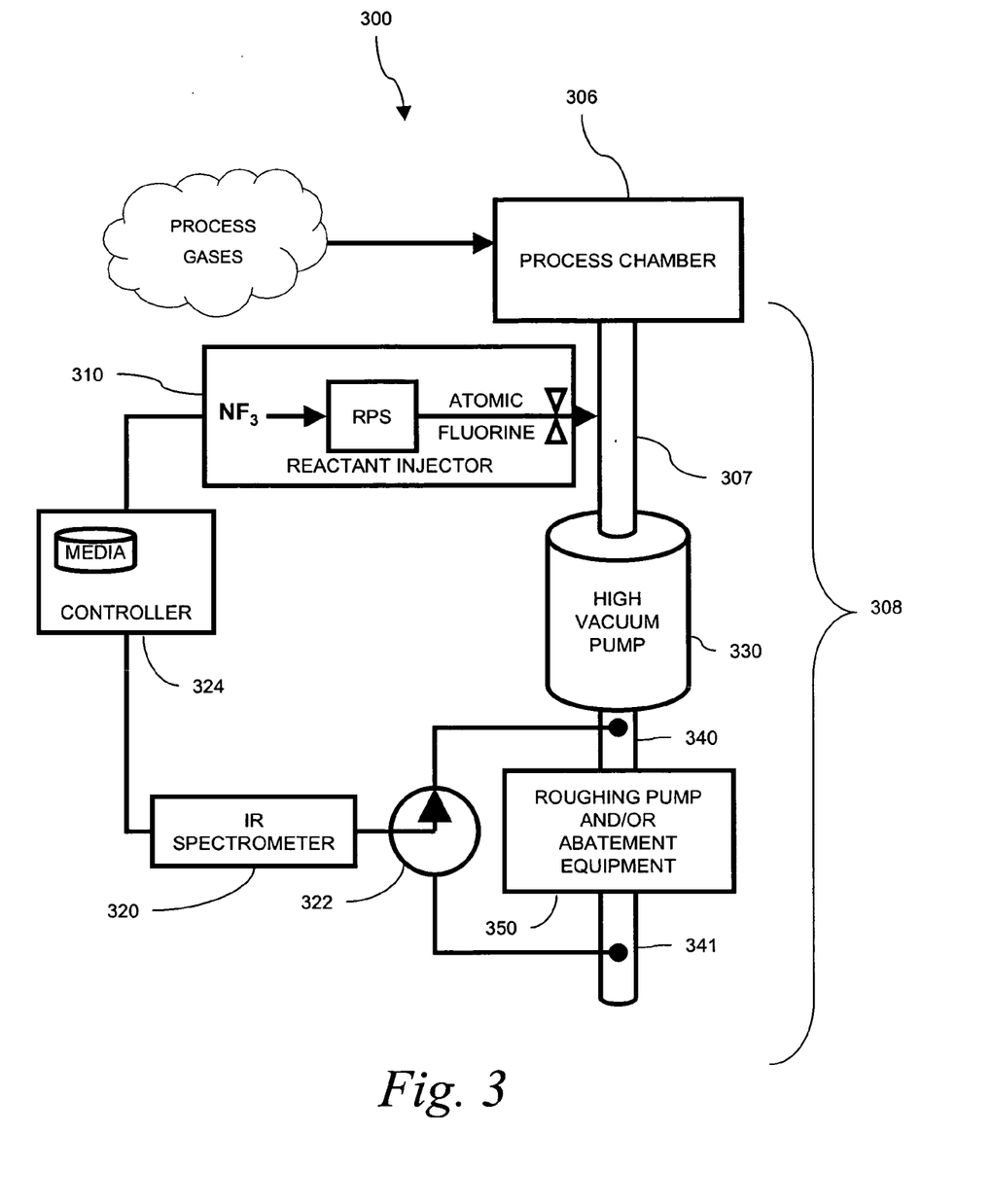
FIG. 3 is a schematic representation of a system according to another embodiment of the invention.

Also shown in FIG. 3 is the use of a single sensor 320 for measuring gas phase concentration in both passageways 340, 341. A switching mechanism 322 alternatively provides a sample of the contents of the passageways 340, 341 to the single sensor 320.

Returning to FIG. 2, logic for the programmable controller 224 such as that described above is stored as executable steps on a readable media 225, which may be integrated in the controller 224, as shown, or may be remote. Logic instructions are read from the media 225 and executed by the controller 224.

Figure 4:
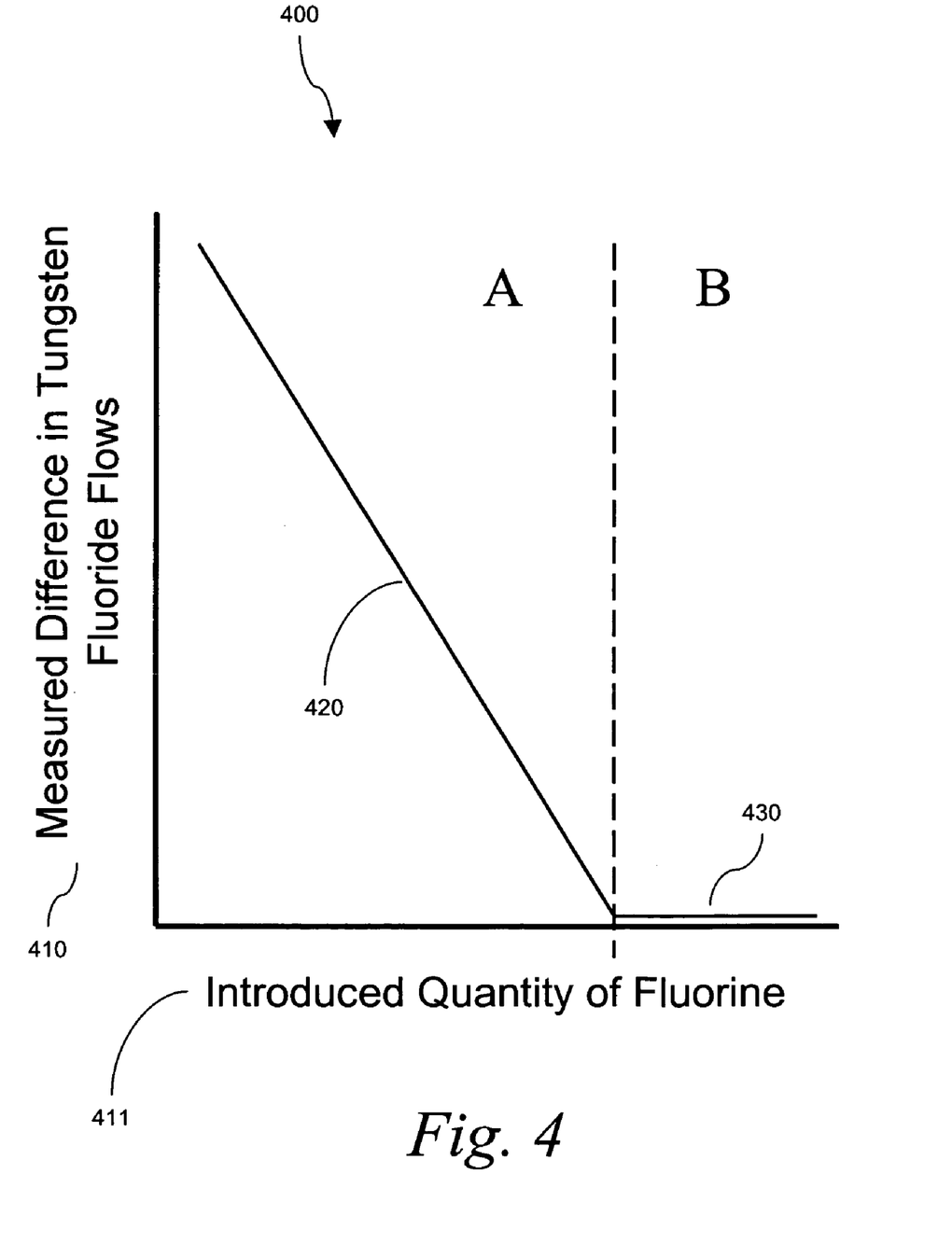
FIG. 4 is a chart showing a relationship between process gas deposition and reactant gas introduction.

A schematic plot 400, shown in FIG. 4, illustrates an inverse relationship between quantities plotted on two axes 410, 411 of the plot. The vertical axis 410 represents a measured difference in tungsten fluoride flows upstream and downstream of the turbomolecular pump. The horizontal axis 411 represents an introduced quantity of fluorine. The plot 400 does not represent actual data, but is instead intended to demonstrate overall behavior of the system.

In region A, it can be seen from the line 420 that an increase in the introduced quantity of fluorine 411 results in a decrease in the difference in tungsten fluoride flows 410. That indicates that the increased fluorine inhibits reactions in the device that cause deposits and consume tungsten fluoride. Once the consumption of tungsten fluoride in the device is close to zero (line 430), as is the case in region B, increasing the quantity of injected reactant gas does not have a strong effect on the measured difference in $WF_6$ flow.

Ideally, the system is operated in a steady state wherein the introduced quantity of fluorine is at the line between regions A & B, which is where a minimum quantity of fluorine is introduced while still preventing deposits in the device. In practice, an acceptable excess quantity of fluorine must be tolerated in order to assure that deposition is completely suppressed. For example, a 5% overshoot of fluorine injection may be set as the acceptable level.

It can furthermore be seen from the plot 400 of FIG. 4 that, in region B, an excess supply of fluorine cannot easily be detected by monitoring the difference in the tungsten fluoride flows across the pump. Instead, other techniques well known in the art are used to determine the location of the ideal range of fluorine injection.

Figure 5:
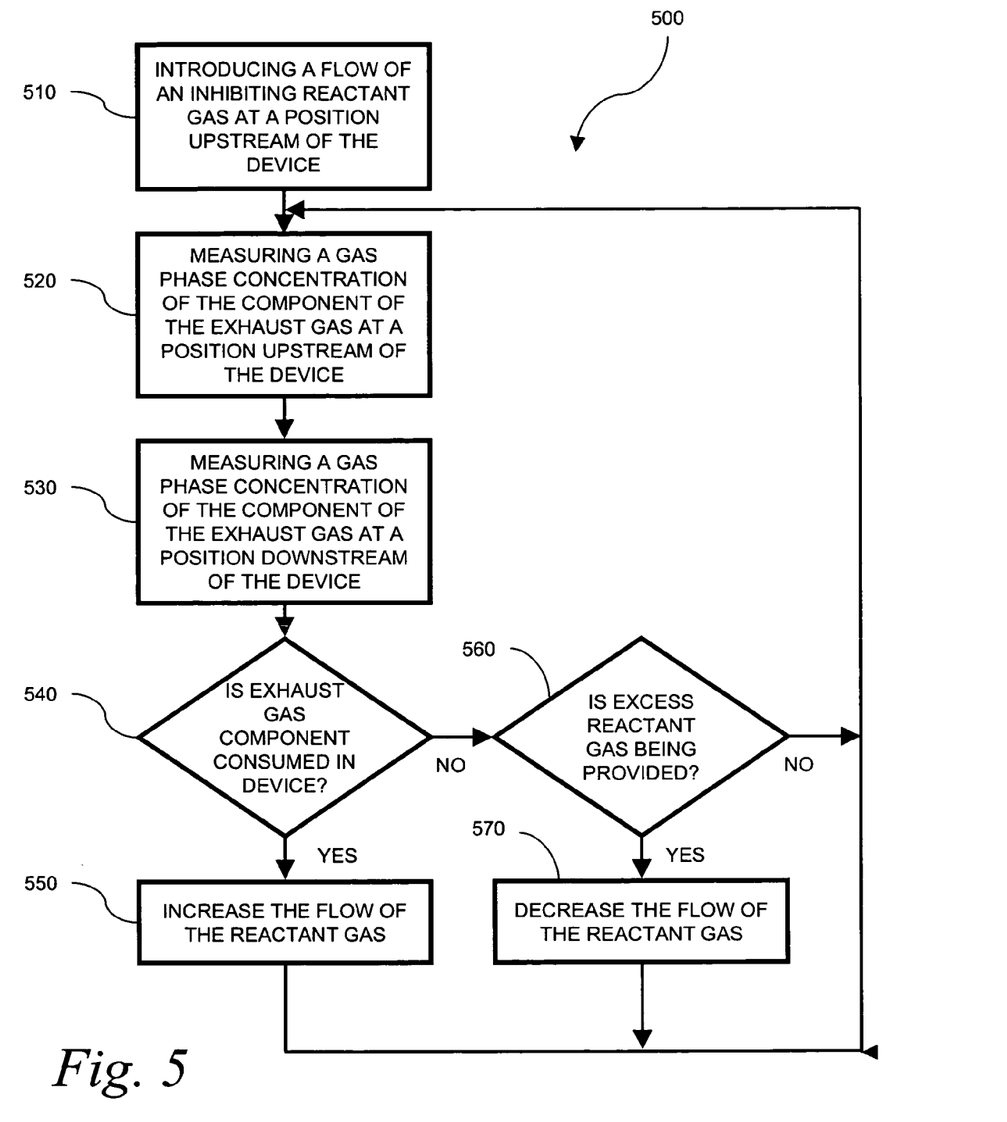
FIG. 5 is a flow chart showing a method according to one embodiment of the invention.

A method 500 in accordance with the invention is shown in flow chart form in FIG. 5. The method is for controlling deposits in a device in a vacuum processing system exhaust path. The deposits are made by one or more components of an exhaust process gas flowing through the path.

Initially, a flow of a reactant gas is introduced (step 510) into the vacuum processing system exhaust path at a position upstream of the device. The reactant gas inhibits the deposits made by the exhaust gas component. It is noted that that initial step is not necessarily done at start-up; i.e., the process may be initialized without any reactant gas flowing, and the reactant gas is started only after a first loop of the method is completed.

A quantity of the component of the exhaust gas present is measured at a position upstream of the device (step 520), and at a position downstream of the device (step 530). In a preferred embodiment, the quantity is measured by an infrared spectrometer as a gas phase concentration. Next, from the upstream and downstream measurements, it is determined (step 540) whether a portion of the exhaust gas component is consumed in the device. If so (i.e., more of the component flows into the device than flows out of the device), then the flow of the reactant gas is increased (step 550), and the method returns to the measuring steps.

If the upstream and downstream measurements show that substantially none of the component of the exhaust gas is consumed in the device (i.e., the flow of exhaust gas component out of the device is equal to or exceeds the flow into the device), and it may be concluded that excess reactant gas is flowing through the device (step 560), then the flow of reactant gas is decreased (step 570) and the program returns to the measuring steps. If the measuring steps show that the exhaust gas component is not being consumed in the device, and there is no excess reactant being provided (i.e., no more than 5% of that required) then no adjustment in reactant gas is made and program control loops to the measuring steps.

In another embodiment of the invention, the technique uses a concentration of a new species formed downstream of the reactant injector, as an indicator of the activity of the reactant. As the amount of injected reactant increases, the formation of the new species increases as well, until another component of the new species is substantially fully consumed. At that point, the concentration of the new species plateaus.

Figure 6:
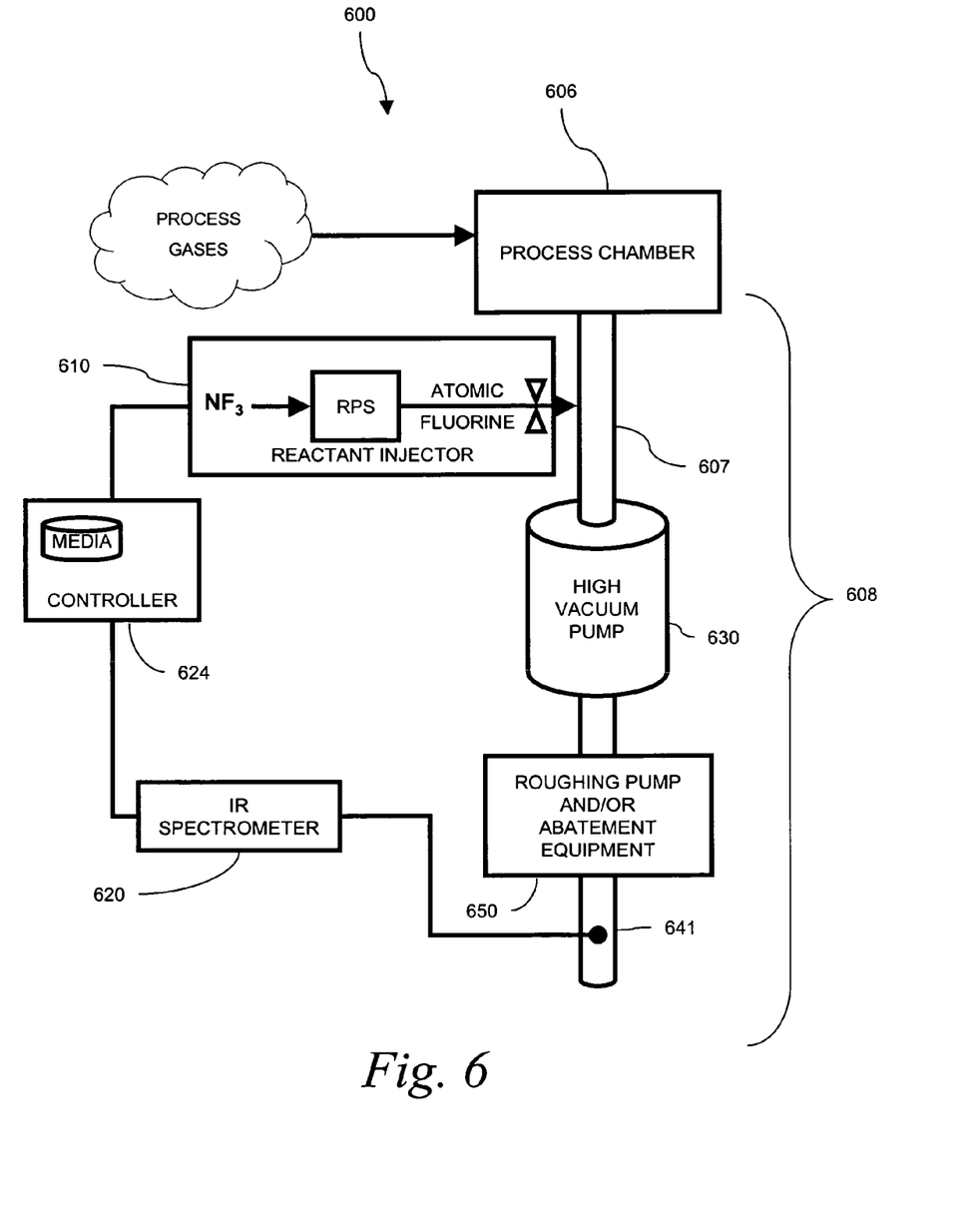
FIG. 6 is a schematic representation of a system according to another embodiment of the invention.

An apparatus 600 according to that embodiment of the invention is shown in FIG. 6. Process gases pass through the process chamber 606, high vacuum pump 630 and additional equipment 650. A reactant gas such as fluorine is injected by the reactant injector 610 at the point 607. Gas is sampled only at the point 641, and is analyzed by the IR spectrometer 620 or by other analysis means. It should be noted that the sample point 641 may be any point in the vacuum exhaust path 608 downstream of the component in which deposition is being controlled.

The reactant gas concentration is increased until a measured concentration of the new species at point 641 stops increasing. At that point, sufficient reactant gas is being introduced to fully consume at least one component of the new species, and introducing additional reactant gas would not additionally suppress deposition.

The foregoing Detailed Description and accompanying figures are to be understood as being in every respect illustrative and exemplary, but not restrictive, and the scope of the invention disclosed herein is not to be determined from the Description of the Invention, but rather from the Claims as interpreted according to the full breadth permitted by the patent laws. For example, while the system is described in connection with suppressing the deposition of tungsten metal in turbomolecular pumps, the system may be used to limit accumulation of other materials on components of a vacuum processing system, such as the deposition of oxides, nitrides, silicides, borides or other ternary or quaternary solid materials. It is to be understood that the embodiments shown and described herein are only illustrative of the principles of the present invention and that various modifications may be implemented by those skilled in the art without departing from the scope and spirit of the invention.

What is claimed is:

1. A method for controlling deposits made by at least one component of an exhaust gas on a device in a vacuum processing system exhaust path, the method comprising the steps of:
   introducing a flow of a reactant gas into the vacuum processing system exhaust path at a position upstream of the device, the reactant gas inhibiting the deposits made by the at least one component of the exhaust gas;
   measuring a quantity of the at least one component of the exhaust gas present at a position upstream of the device;
   measuring a quantity of the at least one component of the exhaust gas present at a position downstream of the device;
   determining from the upstream and downstream measurements whether at least a predetermined portion of the at least one component of the exhaust gas is consumed in the device; and, if so;
   increasing the flow of the reactant gas.

2. The method of claim 1, further comprising the steps of
   determining from the upstream and downstream measurements whether substantially none of the at least one component of the exhaust gas is consumed in the device; and, if so,
   determining whether excess reactant gas is flowing through the device; and, if so,
   decreasing the flow of reactant gas.

3. The method of claim 1, wherein the measuring steps comprise measuring the quantity of the at least one component of the exhaust gas using an instrument selected from the group consisting of an infrared spectrometer, a Raman Spectrometer, a mass spectrometer and a laser induced fluorescence spectrometer.

4. The method of claim 1, wherein the reactant gas is fluorine.

5. The method of claim 1, wherein the step of introducing a flow of a reactant gas into the vacuum processing system exhaust path further comprises dissociating a precursor gas using a remote plasma source.

6. The method of claim 5, wherein the reactant gas is fluorine and the precursor gas is $NF_3$.

7. The method of claim 1, wherein the device is selected from a group consisting of a vacuum pump and an abatement device.

8. The method of claim 1, wherein the at least one component of the exhaust gas is tungsten fluoride.

9. The method of claim 8, wherein the reactant gas is fluorine.

10. The method of claim 1, wherein the at least one component of the exhaust gas comprises at least one gas selected from the group consisting of $WF_3$, $H_2$, $NH_3$, $B_2H_6$ and $SiH_4$.

11. The method of claim 1, wherein the measuring steps comprise measuring a gas phase concentration of the at least one component.

* * * * *